United States Patent [19]
Loftin

[11] 3,935,856
[45] Feb. 3, 1976

[54] SHOE AND FOOT WARMER
[75] Inventor: Wayne M. Loftin, Pasadena, Tex.
[73] Assignee: The Raymond Lee Organization, Inc., New York, N.Y.; a part interest
[22] Filed: Jan. 14, 1975
[21] Appl. No.: 540,991

[52] U.S. Cl. .............................. 126/208
[51] Int. Cl.² ........................... A61F 7/06
[58] Field of Search ............. 126/204, 208

[56] References Cited
UNITED STATES PATENTS

| 38,271 | 4/1863 | Ackley | 126/208 |
| 48,601 | 7/1865 | Taft | 126/207 |
| 701,756 | 6/1902 | McAbee | 126/208 |

*Primary Examiner*—Carroll B. Dority, Jr.
*Attorney, Agent, or Firm*—Howard I. Podell

[57] ABSTRACT

A shoe and foot warmer, heated by the combustion of a liquid fuel, which is attached as a cap to cover toe section of a shoe by means of straps and buckles. Control over the combustion process is exerted by means of a valve controlling the amount of fuel vapor admitted into the combustion section of the device.

3 Claims, 7 Drawing Figures

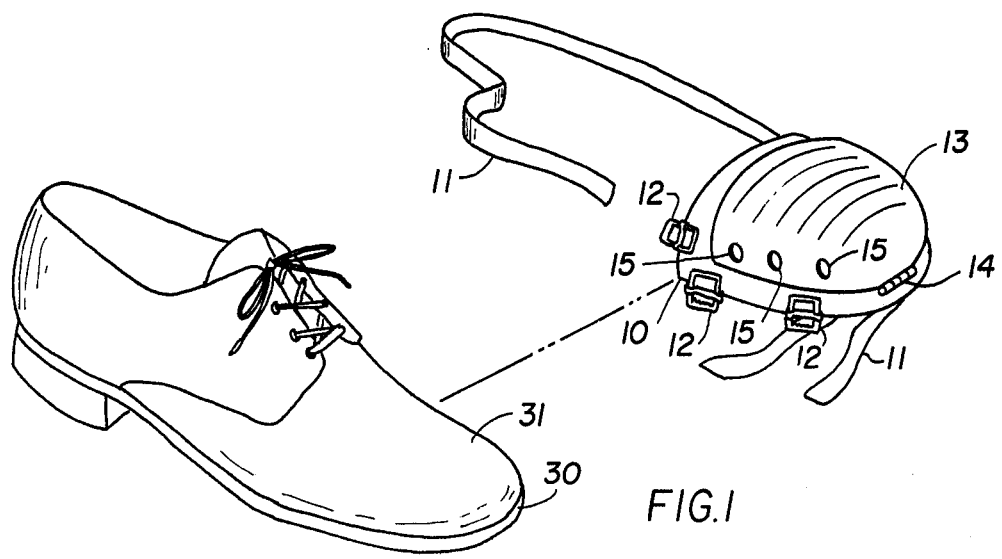
FIG.1
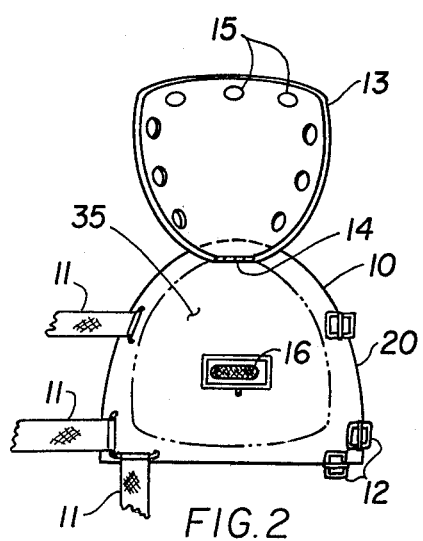
FIG.2
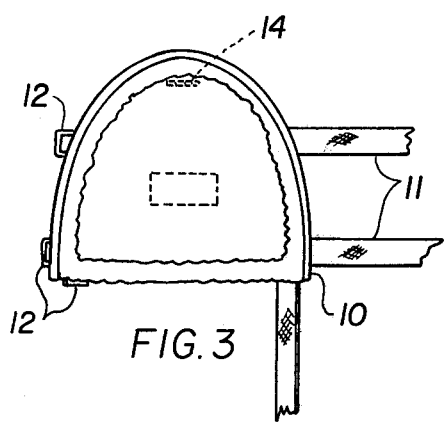
FIG.3
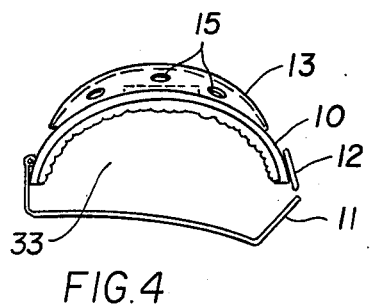
FIG.4
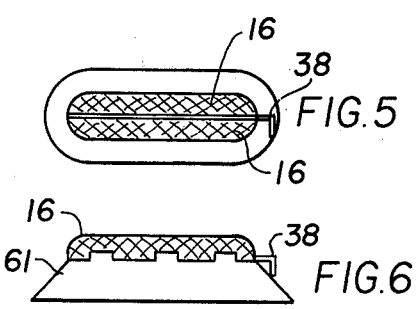
FIG.5
FIG.6
FIG.7

SHOE AND FOOT WARMER

SUMMARY OF THE INVENTION

My invention relates to a shoe and foot warmer, and particularly to a foot fitted as a cap, externally over the toe section of a shoe which is held in place by straps and buckles. An asbestos wick, fueled by a liquid fuel contained in a cotton filled enclosure is fitted in a combustion chamber, with a damper controlling the entry of fuel vapor into the combustion chamber.

BRIEF DESCRIPTION OF THE DRAWINGS

The objects and features of the invention may be understood with reference to the following detailed description of an illustrative embodiment of the invention, taken together with the accompanying drawings in which:

FIG. 1 is an exploded perspective view of the invention and a shoe on which it is to be mounted;

FIG. 2 is a top view of the invention with cover open;

FIG. 3 is a bottom view of the invention with the cover closed;

FIG. 4 is an end sectional view of the invention;

FIG. 5 is a top view of the heating element;

FIG. 6 is a side view of the heating element; and

FIG. 7 is a side view of the damper.

DESCRIPTION OF THE PREFERRED EMBODIMENT

Turning now descriptively to the drawings, in which similar reference characters denote similar elements throughout the several views, FIG. 1 shows the heater unit 10 which fastens over the toe cap section 31 of a shoe 30 by means of attached straps 11 and buckles 12.

As shown in FIGS. 1–4, the heater unit 10 is formed with a hinged metal external cap 13 mounted by forward hinge 14 to the metal base unit 20, which is shaped with a lower concave recess 33 to fit about the shoe toe cap 31. Hinged cap 13 is fitted with perforations 15 to ventilate the combustion chamber section 35 between the hinged cap 13 and the top of the base unit 20.

As shown in FIGS. 2 and 5–7, the heating element is formed of an asbestos wick 16 mounted in a tapered holder 61. Tapered holder 61 mounts on top of unit base 20. Unit base 20 is filled with cotton which holds, by saturation, the liquid fuel. A rotary damper valve 38 fits between wick 16 and base unit 20, to regulate the amount of fuel vapors reaching the wick 16, since wick 16 is not in direct contact with the liquid fuel in base 20.

In operation, the hinged cap 13 is opened and the wick 16 ignited to emit a steady glow. The cap 13 is closed and the heat from the device warms the toe cap of the attached shoe 30.

Since obvious changes may be made in the specific embodiment of the invention described herein, such modifications being within the spirit and scope of the invention claimed, it is indicated that all matter contained herein is intended as illustrative and not as limiting in scope.

Having thus described the invention, what I claim as new and desire to secure by Letters Patent of the United States is:

1. A device for warming a shoe to which it is externally mounted comprising
   a base unit of a size to fit about the toe cap of a shoe with means to attach the base unit to a shoe,
   a cover hinged to the top section of the base cap, enclosing a heater section fitted in the base unit below the hinged cover.

2. The combination as recited in claim 1 in which the heater section comprises a wick mounted above fuel tank.

3. The combination as recited in claim 2 together with control means to regulate the heat developed in operation of the heater unit.

* * * * *